(12) United States Patent
Czarnik

(10) Patent No.: US 8,669,268 B2
(45) Date of Patent: Mar. 11, 2014

(54) DEUTERIUM-ENRICHED PRASUGREL

(75) Inventor: Anthony W Czarnik, Reno, NV (US)

(73) Assignee: DeuteRx, LLC, Andover, MA (US)

( * ) Notice: Subject to any disclaimer, the term of this patent is extended or adjusted under 35 U.S.C. 154(b) by 953 days.

(21) Appl. No.: 12/196,989

(22) Filed: Aug. 22, 2008

(65) Prior Publication Data

US 2009/0069369 A1  Mar. 12, 2009

Related U.S. Application Data

(60) Provisional application No. 60/971,902, filed on Sep. 12, 2007.

(51) Int. Cl.
*A61K 31/4365* (2006.01)
*C07D 495/04* (2006.01)

(52) U.S. Cl.
USPC ............................................. 514/300; 546/114

(58) Field of Classification Search
USPC ........................................... 546/114; 514/300
See application file for complete search history.

(56) References Cited

U.S. PATENT DOCUMENTS

| | | | | |
|---|---|---|---|---|
| 4,421,865 A | * | 12/1983 | Shen | 521/31 |
| 5,149,820 A | * | 9/1992 | Borretzen et al. | 548/215 |
| 5,288,726 A | | 2/1994 | Koike et al. | |
| 5,436,242 A | | 7/1995 | Koike et al. | |
| 5,874,581 A | | 2/1999 | Ataka et al. | |
| 6,334,997 B1 | * | 1/2002 | Foster et al. | 424/1.81 |
| 2004/0253180 A1 | * | 12/2004 | Foster et al. | 424/9.2 |

FOREIGN PATENT DOCUMENTS

WO     26325 A2    10/1995

OTHER PUBLICATIONS

Sugidachi et al., "The greater in vivo, etc.," Journal of Thrombosis and Haemostasis, 5:1545-1551 2007.*
Husted. "New developments, etc.," European Heart Journal Supplements (2007) 9 (Supplement D), D20-D27.*
Smith et al., "Disposition and metabolic, etc.," Xenobiotica, Aug. 2007; 37(8):884-901.*
Farid et al. I, "Cytochrome P450, etc.," Clinical Pharmacology & Therapeutics, 81(5), May 2007, 735-741.*
Farid et al. II, "The disposition of Prasugrel, etc.," Drug Metabolism and Disposition 35:1096-1104, 2007.*
Fisher et al., "The complexities, etc.," Current Opinion in Drug Discovery & Development 2006 9(1) 101-109.*
Wade et al. "Deuterium isotope, etc.," Chemico-Biological Interactions 117 (1999) 191-217.*
Foster, Deuterium isotope, etc., TIPS, Dec. 1984, 524-527.*
Kushner, D.J.; Pharmacological Uses and Perspectives of Heavy Water and Deuterated Compounds; Canadian Journal of Physiology and Pharmacology 1999, 77(2), 79-88.
Yamamoto, T. et al., Synthesis and Configurational Stability of (S)- and (R)-Deuteriuthalidomides. Chem. Pharm. Bull. 2010, 58(1), 110-112.

* cited by examiner

*Primary Examiner* — Patricia L Morris
(74) *Attorney, Agent, or Firm* — Goodwin Procter LLP

(57) ABSTRACT

The present application describes deuterium-enriched prasugrel, pharmaceutically acceptable salt forms thereof, and methods of treating using the same.

10 Claims, No Drawings

DEUTERIUM-ENRICHED PRASUGREL

CROSS-REFERENCE TO RELATED APPLICATIONS

The present application claims priority benefit under 35 U.S.C. §119(e) of U.S. Provisional Patent Application Ser. No. 60/971,902 filed 12 Sep. 2007. The disclosure of this application is incorporated herein by reference.

FIELD OF THE INVENTION

This invention relates generally to deuterium-enriched prasugrel, pharmaceutical compositions containing the same, and methods of using the same.

BACKGROUND OF THE INVENTION

Prasugrel, shown below, is a well known novel platelet inhibitor.

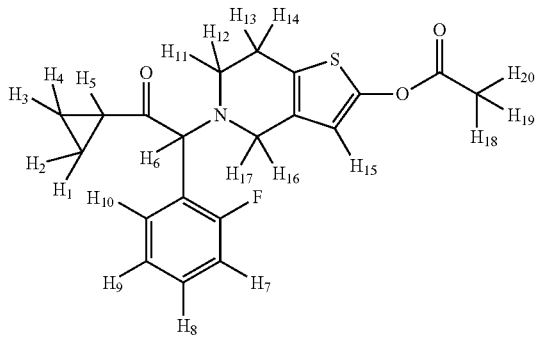

Since prasugrel is a known and useful pharmaceutical, it is desirable to discover novel derivatives thereof. Prasugrel is described in U.S. Pat. Nos. 5,288,726, 5,436,242, and 5,874,581; the contents of which are incorporated herein by reference.

SUMMARY OF THE INVENTION

Accordingly, one object of the present invention is to provide deuterium-enriched prasugrel or a pharmaceutically acceptable salt thereof.

It is another object of the present invention to provide pharmaceutical compositions comprising a pharmaceutically acceptable carrier and a therapeutically effective amount of at least one of the deuterium-enriched compounds of the present invention or a pharmaceutically acceptable salt thereof.

It is another object of the present invention to provide a method for treating percutaneous coronary intervention, comprising administering to a host in need of such treatment a therapeutically effective amount of at least one of the deuterium-enriched compounds of the present invention or a pharmaceutically acceptable salt thereof.

It is another object of the present invention to provide a novel deuterium-enriched prasugrel or a pharmaceutically acceptable salt thereof for use in therapy.

It is another object of the present invention to provide the use of a novel deuterium-enriched prasugrel or a pharmaceutically acceptable salt thereof for the manufacture of a medicament (e.g., for the treatment of percutaneous coronary intervention).

These and other objects, which will become apparent during the following detailed description, have been achieved by the inventor's discovery of the presently claimed deuterium-enriched prasugrel.

DETAILED DESCRIPTION OF PREFERRED EMBODIMENTS

Deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their non-enriched counterparts.

All percentages given for the amount of deuterium present are mole percentages.

It can be quite difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enriched can be achieved by either exchanging protons with deuterium or by synthesizing the molecule with enriched starting materials.

The present invention provides deuterium-enriched prasugrel or a pharmaceutically acceptable salt thereof. There are twenty hydrogen atoms in the prasugrel portion of prasugrel as show by variables $R_1$-$R_{20}$ in formula I below.

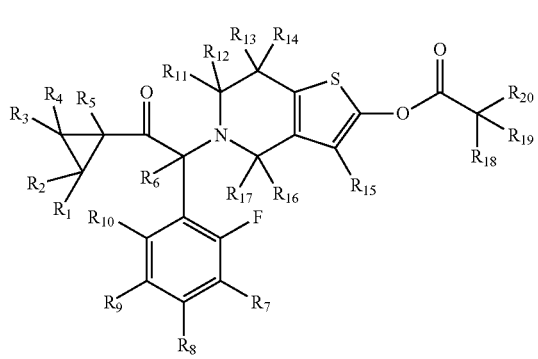

The hydrogens present on prasugrel have different capacities for exchange with deuterium. The hydrogen atoms of prasugrel are not easily exchangeable for deuterium atoms. However, deuterium atoms may be incorporated by the use of deuterated starting materials or intermediates during the construction of prasugrel.

The present invention is based on increasing the amount of deuterium present in prasugrel above its natural abundance. This increasing is called enrichment or deuterium-enrichment. If not specifically noted, the percentage of enrichment refers to the percentage of deuterium present in the compound, mixture of compounds, or composition. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Since there are 20 hydrogens in prasugrel, replacement of a single hydrogen atom with deuterium would result in a molecule with about 5% deuterium enrichment. In order to achieve enrichment less than about 5%, but above the natural abundance, only partial deuteration of one site is required. Thus, less than about 5% enrichment would still refer to deuterium-enriched prasugrel.

With the natural abundance of deuterium being 0.015%, one would expect that for approximately every 6,667 molecules of prasugrel (1/0.00015=6,667), there is one naturally occurring molecule with one deuterium present. Since prasugrel has 20 positions, one would roughly expect that for approximately every 133,340 molecules of prasugrel (20×6,667), all 20 different, naturally occurring, mono-deuterated prasugrels would be present. This approximation is a rough estimate as it doesn't take into account the different exchange rates of the hydrogen atoms on prasugrel. For naturally occurring molecules with more than one deuterium, the numbers become vastly larger. In view of this natural abundance, the present invention, in an embodiment, relates to an amount of an deuterium enriched compound, whereby the enrichment recited will be more than naturally occurring deuterated molecules.

In view of the natural abundance of deuterium-enriched prasugrel, the present invention also relates to isolated or purified deuterium-enriched prasugrel. The isolated or purified deuterium-enriched prasugrel is a group of molecules whose deuterium levels are above the naturally occurring levels (e.g., 5%). The isolated or purified deuterium-enriched prasugrel can be obtained by techniques known to those of skill in the art (e.g., see the syntheses described below).

The present invention also relates to compositions comprising deuterium-enriched prasugrel. The compositions require the presence of deuterium-enriched prasugrel which is greater than its natural abundance. For example, the compositions of the present invention can comprise (a) a μg of a deuterium-enriched prasugrel; (b) a mg of a deuterium-enriched prasugrel; and, (c) a gram of a deuterium-enriched prasugrel.

In an embodiment, the present invention provides an amount of a novel deuterium-enriched prasugrel.

Examples of amounts include, but are not limited to (a) at least 0.01, 0.02, 0.03, 0.04, 0.05, 0.1, 0.2, 0.3, 0.4, 0.5, to 1 mole, (b) at least 0.1 moles, and (c) at least 1 mole of the compound. The present amounts also cover lab-scale (e.g., gram scale), kilo-lab scale (e.g., kilogram scale), and industrial or commercial scale (e.g., multi-kilogram or above scale) quantities as these will be more useful in the actual manufacture of a pharmaceutical. Industrial/commercial scale refers to the amount of product that would be produced in a batch that was designed for clinical testing, formulation, sale/distribution to the public, etc.

In another embodiment, the present invention provides a novel, deuterium enriched compound of formula I or a pharmaceutically acceptable salt thereof.

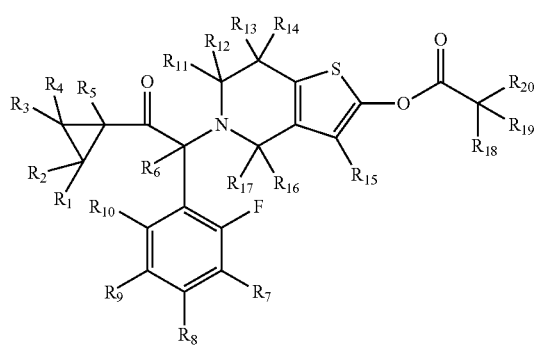

I wherein $R_1$-$R_{20}$ are independently selected from H and D; and the abundance of deuterium in $R_1$-$R_{20}$ is at least 5%. The abundance can also be (a) at least 10%, (b) at least 15%, (c) at least 20%, (d) at least 25%, (e) at least 30%, (f) at least 35%, (g) at least 40%, (h) at least 45%, (i) at least 50%, (j) at least 55%, (k) at least 60%, (l) at least 65%, (m) at least 70%, (n) at least 75%, (o) at least 80%, (p) at least 85%, (q) at least 90%, (r) at least 95%, and (s) 100%.

In another embodiment, the present invention provides a novel, deuterium enriched compound of formula I or a pharmaceutically acceptable salt thereof, wherein the abundance of deuterium in $R_1$-$R_5$ is at least 20%. The abundance can also be (a) at least 40%, (b) at least 60%, (c) at least 80%, and (d) 100%.

In another embodiment, the present invention provides a novel, deuterium enriched compound of formula I or a pharmaceutically acceptable salt thereof, wherein the abundance of deuterium in $R_6$ is at least 100%.

In another embodiment, the present invention provides a novel, deuterium enriched compound of formula I or a pharmaceutically acceptable salt thereof, wherein the abundance of deuterium in $R_7$-$R_{10}$ is at least 25%. The abundance can also be (a) at least 50%, (b) at least 75%, and (c) 100%.

In another embodiment, the present invention provides a novel, deuterium enriched compound of formula I or a pharmaceutically acceptable salt thereof, wherein the abundance of deuterium in $R_{11}$-$R_{17}$ is at least 14%. The abundance can also be (a) at least 29%, (b) at least 43%, (c) at least 57%, (d) at least 71%, (e) at least 86%, and (f) 100%.

In another embodiment, the present invention provides a novel, deuterium enriched compound of formula I or a pharmaceutically acceptable salt thereof, wherein the abundance of deuterium in $R_{15}$ is at least 100%.

In another embodiment, the present invention provides a novel, deuterium enriched compound of formula I or a pharmaceutically acceptable salt thereof, wherein the abundance of deuterium in $R_{18}$-$R_{20}$ is at least 33%. The abundance can also be (a) at least 67%, and (b) 100%.

In another embodiment, the present invention provides an isolated novel, deuterium enriched compound of formula I or a pharmaceutically acceptable salt thereof.

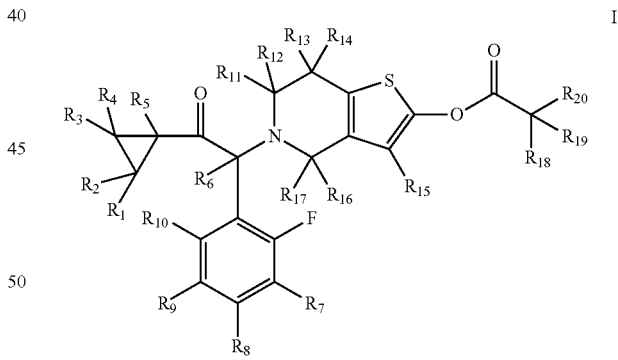

I wherein $R_1$-$R_{20}$ are independently selected from H and D; and the abundance of deuterium in $R_1$-$R_{20}$ is at least 5%. The abundance can also be (a) at least 10%, (b) at least 15%, (c) at least 20%, (d) at least 25%, (e) at least 30%, (f) at least 35%, (g) at least 40%, (h) at least 45%, (i) at least 50%, (j) at least 55%, (k) at least 60%, (l) at least 65%, (m) at least 70%, (n) at least 75%, (o) at least 80%, (p) at least 85%, (q) at least 90%, (r) at least 95%, and (s) 100%.

In another embodiment, the present invention provides an isolated novel, deuterium enriched compound of formula I or a pharmaceutically acceptable salt thereof, wherein the abundance of deuterium in $R_1$-$R_5$ is at least 20%. The abundance can also be (a) at least 40%, (b) at least 60%, (c) at least 80%, and (d) 100%.

In another embodiment, the present invention provides an isolated novel, deuterium enriched compound of formula I or a pharmaceutically acceptable salt thereof, wherein the abundance of deuterium in $R_6$ is at least 100%.

In another embodiment, the present invention provides an isolated novel, deuterium enriched compound of formula I or a pharmaceutically acceptable salt thereof, wherein the abundance of deuterium in $R_7$-$R_{10}$ is at least 25%. The abundance can also be (a) at least 50%, (b) at least 75%, and (c) 100%.

In another embodiment, the present invention provides an isolated novel, deuterium enriched compound of formula I or a pharmaceutically acceptable salt thereof, wherein the abundance of deuterium in $R_{11}$-$R_{17}$ is at least 14%. The abundance can also be (a) at least 29%, (b) at least 43%, (c) at least 57%, (d) at least 71%, (e) at least 86%, and (f) 100%.

In another embodiment, the present invention provides an isolated novel, deuterium enriched compound of formula I or a pharmaceutically acceptable salt thereof, wherein the abundance of deuterium in $R_{15}$ is at least 100%.

In another embodiment, the present invention provides an isolated novel, deuterium enriched compound of formula I or a pharmaceutically acceptable salt thereof, wherein the abundance of deuterium in $R_{18}$-$R_{20}$ is at least 33%. The abundance can also be (a) at least 67%, and (b) 100%.

In another embodiment, the present invention provides novel mixture of deuterium enriched compounds of formula I or a pharmaceutically acceptable salt thereof.

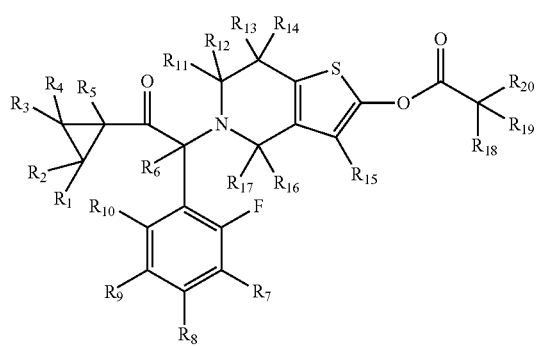

I wherein $R_1$-$R_{20}$ are independently selected from H and D; and the abundance of deuterium in $R_1$-$R_{20}$ is at least 5%. The abundance can also be (a) at least 10%, (b) at least 15%, (c) at least 20%, (d) at least 25%, (e) at least 30%, (f) at least 35%, (g) at least 40%, (h) at least 45%, (i) at least 50%, (j) at least 55%, (k) at least 60%, (l) at least 65%, (m) at least 70%, (n) at least 75%, (o) at least 80%, (p) at least 85%, (q) at least 90%, (r) at least 95%, and (s) 100%.

In another embodiment, the present invention provides a novel mixture of, deuterium enriched compound of formula I or a pharmaceutically acceptable salt thereof, wherein the abundance of deuterium in $R_1$-$R_5$ is at least 20%. The abundance can also be (a) at least 40%, (b) at least 60%, (c) at least 80%, and (d) 100%.

In another embodiment, the present invention provides a novel mixture of, deuterium enriched compound of formula I or a pharmaceutically acceptable salt thereof, wherein the abundance of deuterium in $R_6$ is at least 100%.

In another embodiment, the present invention provides a novel mixture of, deuterium enriched compound of formula I or a pharmaceutically acceptable salt thereof, wherein the abundance of deuterium in $R_7$-$R_{10}$ is at least 25%. The abundance can also be (a) at least 50%, (b) at least 75%, and (c) 100%.

In another embodiment, the present invention provides a novel mixture of, deuterium enriched compound of formula I or a pharmaceutically acceptable salt thereof, wherein the abundance of deuterium in $R_{11}$-$R_{17}$ is at least 14%. The abundance can also be (a) at least 29%, (b) at least 43%, (c) at least 57%, (d) at least 71%, (e) at least 86%, and (f) 100%.

In another embodiment, the present invention provides a novel mixture of, deuterium enriched compound of formula I or a pharmaceutically acceptable salt thereof, wherein the abundance of deuterium in $R_{15}$ is at least 100%.

In another embodiment, the present invention provides a novel mixture of, deuterium enriched compound of formula I or a pharmaceutically acceptable salt thereof, wherein the abundance of deuterium in $R_{18}$-$R_{20}$ is at least 33%. The abundance can also be (a) at least 67%, and (b) 100%.

In another embodiment, the present invention provides novel pharmaceutical compositions, comprising: a pharmaceutically acceptable carrier and a therapeutically effective amount of a deuterium-enriched compound of the present invention.

In another embodiment, the present invention provides a novel method for treating percutaneous coronary intervention comprising: administering to a patient in need thereof a therapeutically effective amount of a deuterium-enriched compound of the present invention.

In another embodiment, the present invention provides an amount of a deuterium-enriched compound of the present invention as described above for use in therapy.

In another embodiment, the present invention provides the use of an amount of a deuterium-enriched compound of the present invention for the manufacture of a medicament (e.g., for the treatment of percutaneous coronary intervention).

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

DEFINITIONS

The examples provided in the definitions present in this application are non-inclusive unless otherwise stated. They include but are not limited to the recited examples.

The compounds of the present invention may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. All processes used to prepare compounds of the present invention and intermediates made therein are considered to be part of the present invention. All tautomers of shown or described compounds are also considered to be part of the present invention.

"Host" preferably refers to a human. It also includes other mammals including the equine, porcine, bovine, feline, and canine families.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Therapeutically effective amount" includes an amount of a compound of the present invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination. Synergy, as described, for example, by Chou and Talalay, Adv. Enzyme Regul. 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

Synthesis

Scheme 1 shows an example of how to prepare prasugrel.

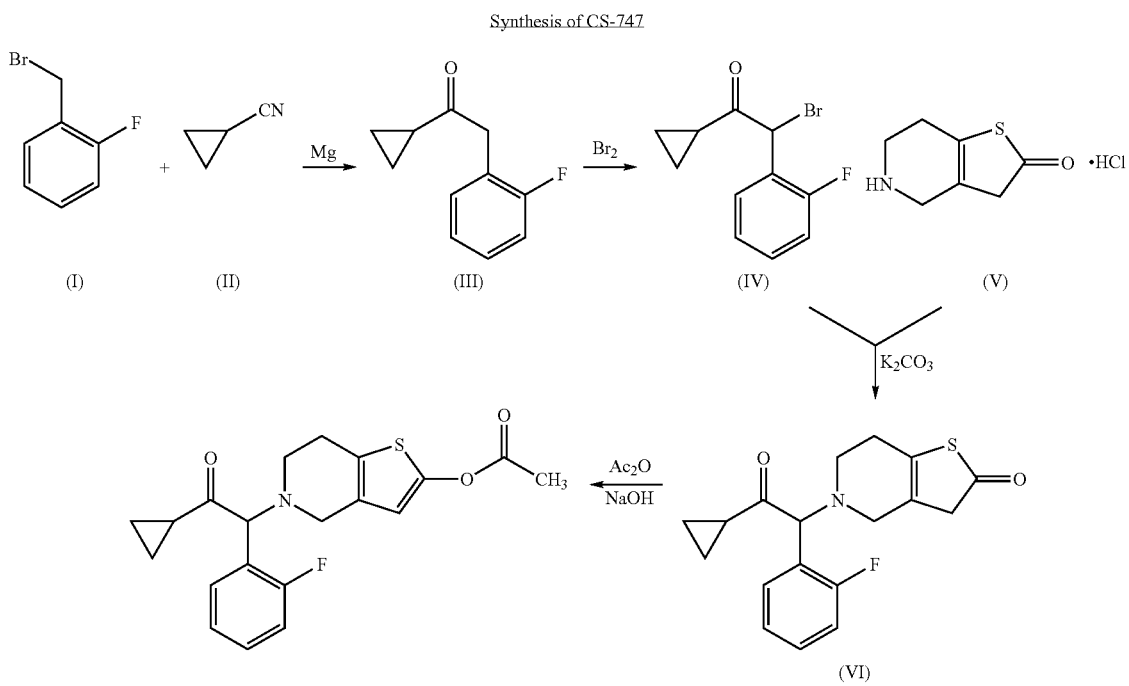

Synthesis of CS-747

Using combinations of various deuterated starting materials and intermediates shown in Scheme 1, a person skilled in the art of organic chemistry should be able to prepare a wide variety of deuterated prasugrel analogs.

EXAMPLES

Table 1 provides compounds that are representative examples of the present invention. When one of $R_1$-$R_{20}$ is present, it is selected from H or D.

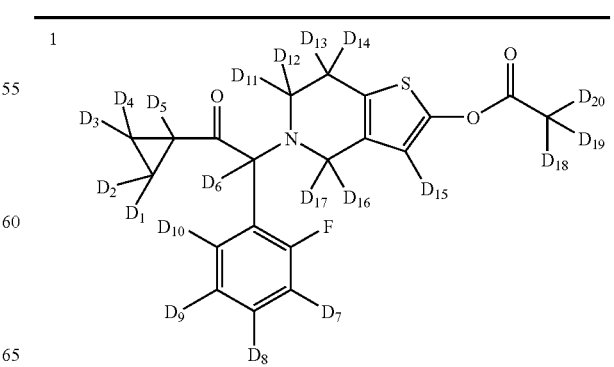

1

-continued
2
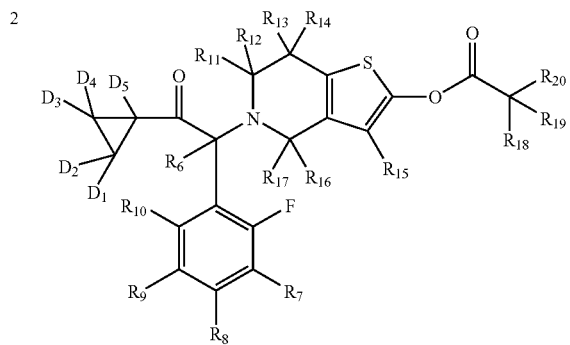
3
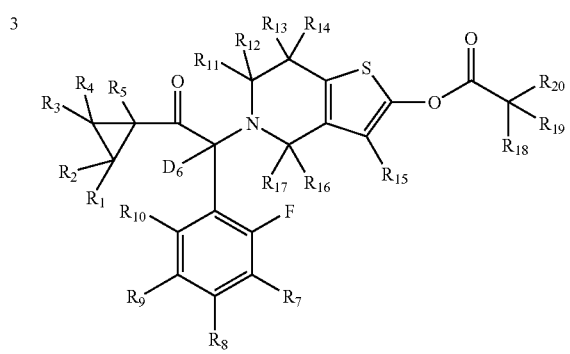
4
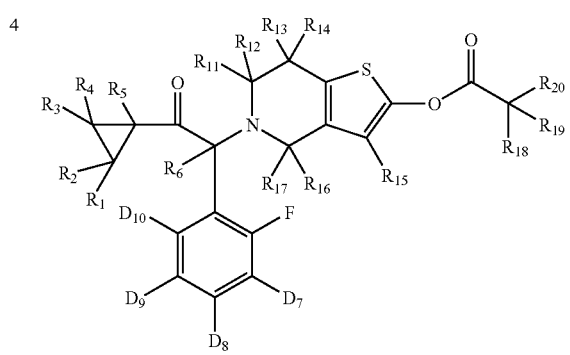
5
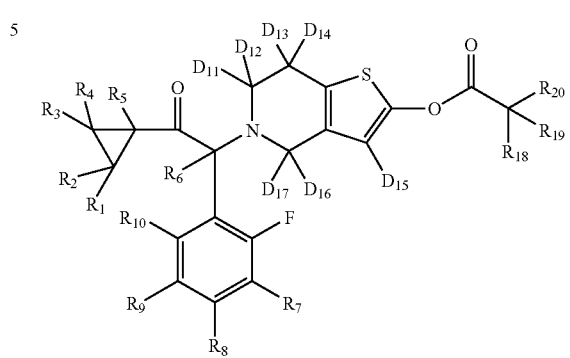
-continued
6
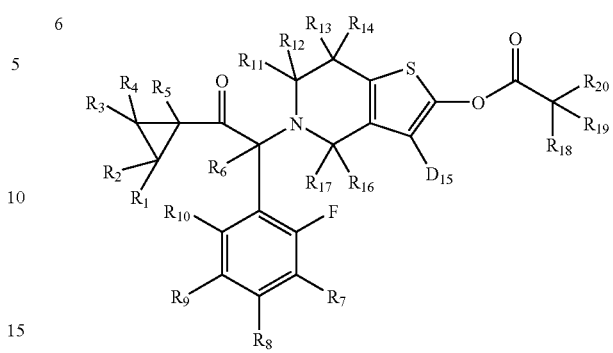
7
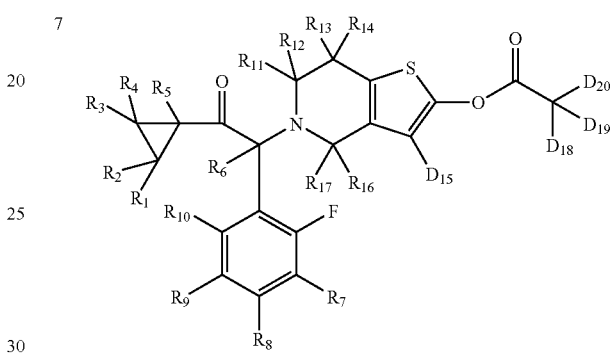
Table 2 provides compounds that are representative examples of the present invention. Where H is shown, it represents naturally abundant hydrogen.
8
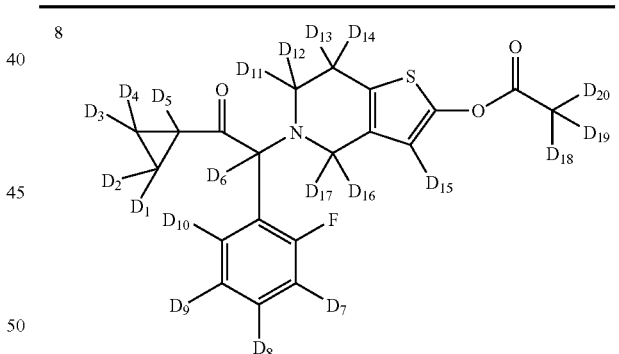
9
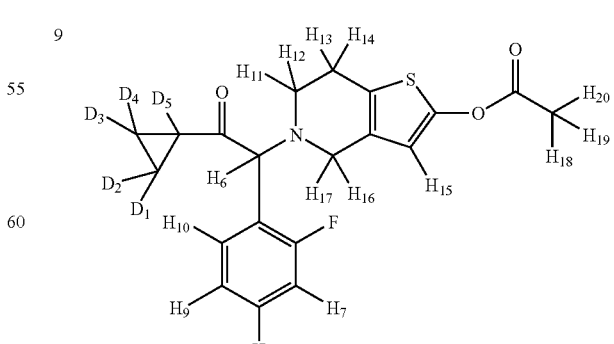

10

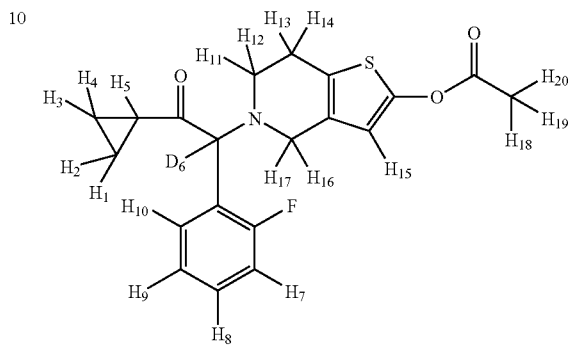

11

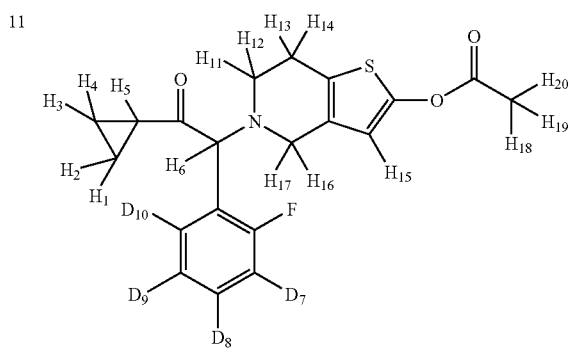

12

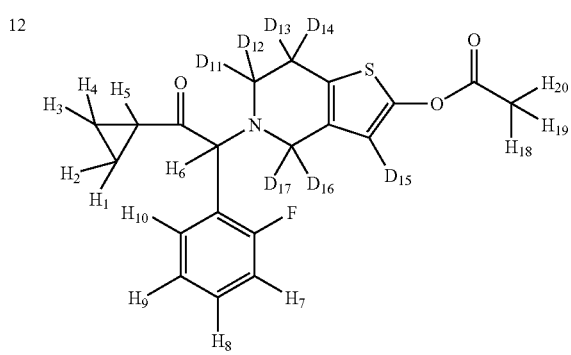

13

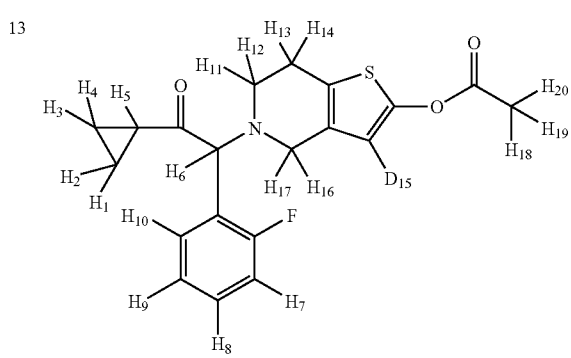

14

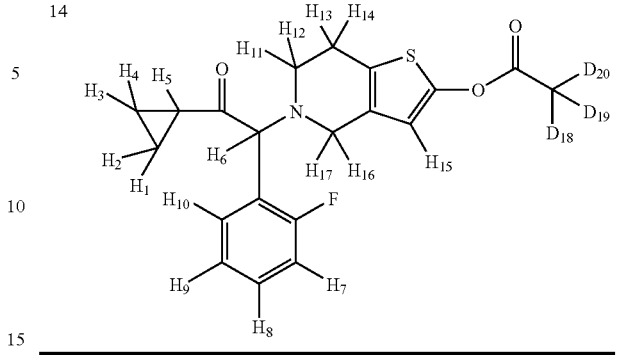

Numerous modifications and variations of the present invention are possible in light of the above teachings. It is therefore to be understood that within the scope of the appended claims, the invention may be practiced otherwise that as specifically described herein.

What is claimed is:

1. A deuterium-enriched compound of formula I or a pharmaceutically acceptable salt thereof:

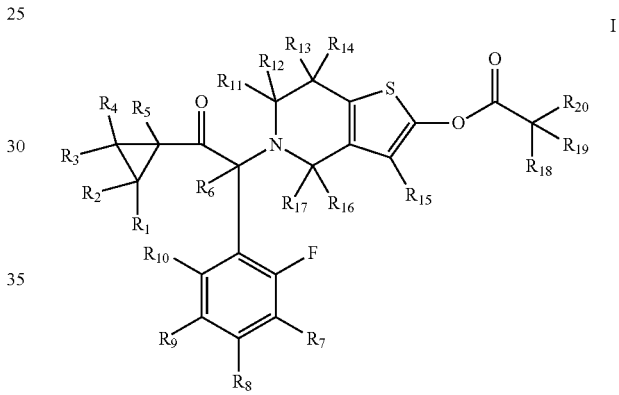

I wherein $R_1$-$R_5$ and $R_7$-$R_{20}$ are H, and $R_6$ is D.

2. A pharmaceutical composition, comprising: a pharmaceutically acceptable carrier and a therapeutically effective amount of a compound of claim 1 or a pharmaceutically acceptable salt form thereof.

3. A method for treating percutaneous coronary intervention comprising: administering, to a patient in need thereof, a therapeutically effective amount of a compound of claim 1 or a pharmaceutically acceptable salt form thereof.

4. A compound of claim 1, wherein the compound is represented by

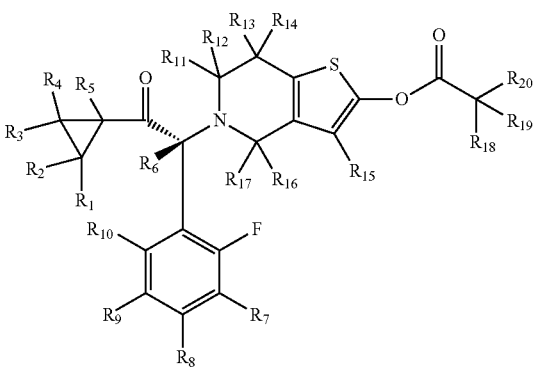

or a pharmaceutically acceptable salt form thereof, wherein $R_1$-$R_5$ and $R_7$-$R_{20}$ are H and $R_6$ is D.

5. A compound of claim 1, wherein the compound is represented by

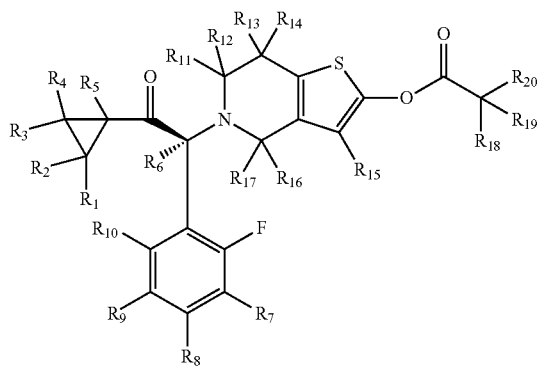

or a pharmaceutically acceptable salt form thereof, wherein $R_1$-$R_5$ and $R_7$-$R_{20}$ are H, and $R_6$ is D.

6. A pharmaceutical composition, comprising a pharmaceutically acceptable carrier and a compound of claim 1.

7. A pharmaceutical composition, comprising a pharmaceutically acceptable carrier and a compound of claim 4.

8. A pharmaceutical composition, comprising a pharmaceutically acceptable carrier and a compound of claim 5.

9. A method for treating percutaneous coronary intervention comprising: administering, to a patient in need thereof, a therapeutically effective amount of a compound of claim 4 to treat said percutaneous coronary intervention.

10. A method for treating percutaneous coronary intervention comprising: administering, to a patient in need thereof, a therapeutically effective amount of a compound of claim 5 to treat said percutaneous coronary intervention.

* * * * *